(12) United States Patent
Pardonge

(10) Patent No.: US 9,387,975 B2
(45) Date of Patent: Jul. 12, 2016

(54) DISTRIBUTION HEAD FOR A DEVICE FOR DISTRIBUTING A FLUID PRODUCT

(75) Inventor: Jean-Marc Pardonge, Les Authieux sur le Port St Ouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 338 days.

(21) Appl. No.: 13/502,926

(22) PCT Filed: Oct. 20, 2010

(86) PCT No.: PCT/FR2010/052235
§ 371 (c)(1),
(2), (4) Date: Apr. 19, 2012

(87) PCT Pub. No.: WO2011/048330
PCT Pub. Date: Apr. 28, 2011

(65) Prior Publication Data
US 2012/0205464 A1 Aug. 16, 2012

(30) Foreign Application Priority Data
Oct. 20, 2009 (FR) ..................................... 09 57337

(51) Int. Cl.
*B05B 1/08* (2006.01)
*B65D 83/28* (2006.01)
*A61M 15/00* (2006.01)
*A61M 15/08* (2006.01)
*B05B 17/06* (2006.01)
*B05B 11/00* (2006.01)

(52) U.S. Cl.
CPC ........... *B65D 83/28* (2013.01); *A61M 15/0085* (2013.01); *A61M 15/08* (2013.01); *B05B 17/0607* (2013.01); *B05B 11/30* (2013.01)

(58) Field of Classification Search
CPC ................ B05B 17/06–17/0669; B05B 11/30; B65D 83/28; A61M 15/0085; A61M 15/08
USPC ............................................ 239/102.1, 120.2
See application file for complete search history.

(56) References Cited

U.S. PATENT DOCUMENTS

| | | | |
|---|---|---|---|
| 3,224,677 A | | 12/1965 | Schmidt et al. |
| 5,435,282 A | * | 7/1995 | Haber et al. ............. 128/200.16 |
| 2007/0119969 A1 | * | 5/2007 | Collins et al. ............. 239/102.1 |
| 2008/0128527 A1 | * | 6/2008 | Chan et al. ........................ 239/4 |
| 2008/0299049 A1 | * | 12/2008 | Stangl ............................. 424/45 |
| 2009/0054116 A1 | * | 2/2009 | Hakunti et al. ............... 455/899 |
| 2009/0108094 A1 | * | 4/2009 | Ivri ................................ 239/101 |

FOREIGN PATENT DOCUMENTS

| | | |
|---|---|---|
| CN | 201139848 Y | 10/2008 |
| DE | 101 02 846 A1 | 8/2002 |
| JP | 8-332425 A | 12/1996 |
| JP | 8-332426 A | 12/1996 |

* cited by examiner

*Primary Examiner* — Arthur O Hall
*Assistant Examiner* — Juan C Barrera
(74) *Attorney, Agent, or Firm* — Sughrue Mion, PLLC

(57) ABSTRACT

A dispenser head for a fluid dispenser device, the head including a hollow body (30, 130, 230) that defines a fluid passage between an inlet orifice (32, 132, 232) and a spray orifice (31, 131, 231); vibration generator means (40, 140, 240) being arranged in said passage upstream from said spray orifice (31, 131, 231), said vibration generator means (40, 140, 240) being actuated while fluid is passing so as to spray said fluid finely through said spray orifice (31, 131, 231).

11 Claims, 2 Drawing Sheets

DISTRIBUTION HEAD FOR A DEVICE FOR DISTRIBUTING A FLUID PRODUCT

The present invention relates to a fluid dispenser device including a dispenser head.

Figure 1:
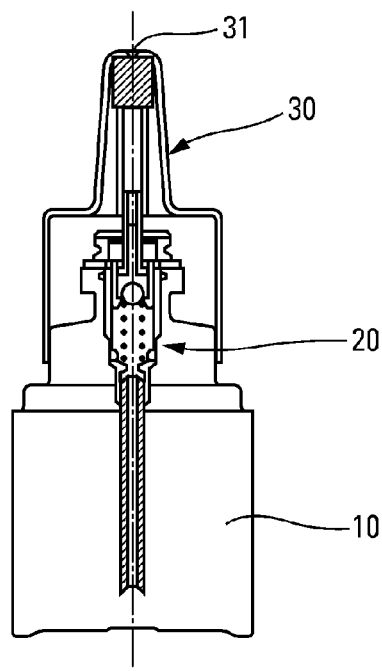
Figure 4:
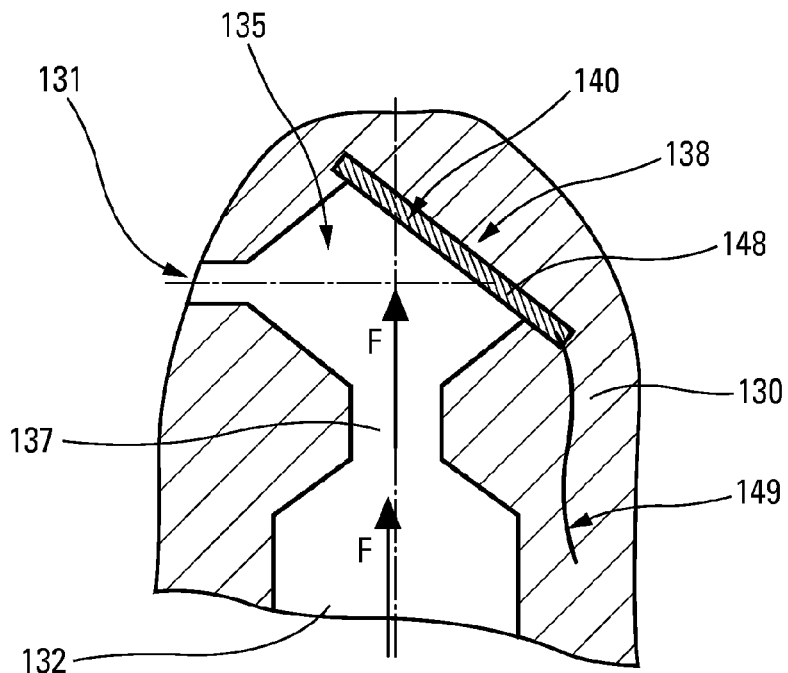

More particularly, the present invention relates to fluid dispenser devices that are suitable for dispensing or spraying doses of biological active principles, e.g. proteins, peptides, hormones, enzymes, or similar. In particular, such dispensing may be performed using a nasal spray. Until now, and in known manner, fluid dispenser devices used in the pharmaceutical industry generally include a reservoir on which there is mounted a pump or a valve that is actuated by means of a pusher or dispenser head provided with a spray orifice. Such devices, that are entirely suitable for dispensing conventional liquids in the pharmaceutical industry, turn out to be more difficult to use for dispensing biological active principles such as proteins, peptides, hormones, enzymes, or similar. In particular, the mechanical and fluidic characteristics provided by the pumps or the valves, and in particular the headlosses, the levels of turbulence, and the shear stresses, are generally found to be incompatible with the three-dimensional molecular structure of said biological active principles. As a result, such biological active principles generally deteriorate while being dispensed through conventional dispenser devices, in particular through spray profiles.

An object of the present invention is to provide a fluid dispenser device including a dispenser head that does not have the above-mentioned drawbacks.

More particularly, an object of the present invention is to provide a dispenser device that is suitable for dispensing biological active principles without causing them to deteriorate in negative manner.

Another object of the present invention is to provide such a fluid dispenser device that is suitable for providing spraying performance that is compatible with the nature of biological active principles such as proteins, peptides, hormones, enzymes, or similar.

Another object of the present invention is to provide such a fluid dispenser device that is simple and inexpensive to manufacture and to assemble.

The present invention thus provides a fluid dispenser device comprising: a reservoir containing fluid; a dispenser member, such as a pump or a valve, that is mounted on said reservoir; and a dispenser head that is mounted on said dispenser member, said dispenser head including a hollow body that defines a fluid passage between an inlet orifice, connected to said dispenser member, and a spray orifice; vibration generator means being arranged in said passage upstream from said spray orifice, said vibration generator means being actuated while fluid is passing so as to spray said fluid finely through said spray orifice.

Advantageously, said vibration generator means include a piezoelectric material.

In an advantageous first embodiment, said vibration generator means include a vibrating pin that includes a tip that is adapted to plug said spray orifice in a closed position.

Advantageously, said inlet orifice and said spray orifice are oriented axially along a longitudinal axis of said head, said pin being movable and vibrating along said longitudinal axis.

Advantageously, in the closed position, said tip co-operates in leaktight manner with a sealing diaphragm that is arranged directly upstream from said spray orifice.

Advantageously, said pin is fastened on a piezoelectric plate.

Advantageously, said pin is axially movable in said head between a closed position in which it plugs the spray orifice and a fluid passage, thereby defining a spray chamber, and an open position in which it opens said spray orifice and said fluid passage, enabling the fluid to pass from said inlet orifice to said spray orifice.

Advantageously, said fluid passage is formed by a portion of greater diameter formed inside said dispenser head.

In an advantageous second embodiment, said vibration generator means comprise a vibrating plate that is arranged on an inside wall of said head, the fluid impacting said vibrating plate.

Advantageously, said outlet orifice is oriented approximately perpendicularly to the direction of flow of the fluid through the inlet orifice, said vibrating plate being arranged on an inside wall that slopes, preferably at about 45°, so that the jet of fluid impacting said vibrating plate is fragmented into spray and directed towards the spray orifice.

Advantageously, said vibrating plate forms a wall of a spray chamber that includes a chamber inlet connected to said inlet orifice, and that is provided with said spray orifice.

In an advantageous third embodiment, said vibration generator means comprise a vibrating diaphragm that defines a resonance chamber between said vibrating diaphragm and the spray orifice.

Advantageously, said resonance chamber is substantially in the shape of a cylinder having a length and a diameter that are shorter than the resonance wavelengths of said diaphragm, said resonance chamber forming a Helmholtz resonator.

Advantageously, said diaphragm has substantially the same diameter as said resonance chamber, said head including a passage for the fluid, which passage extends radially outside said diaphragm.

Advantageously, the fluid spray that is sprayed through said spray orifice has a mean particle size lying in the range 20 micrometers (μm) to 40 μm, and/or a spray speed that is less than 10 meters per second (m/s), advantageously less than 5 m/s, preferably about 1 m/s, and/or a spray angle that is less than 50°, advantageously about 30°.

These characteristics and advantages and others of the present invention appear more clearly from the following detailed description of three embodiments of the present invention, given by way of non-limiting example, and with reference to the accompanying drawings, in which:

FIG. 1 is a diagrammatic section view of a fluid dispenser device to which the present invention may apply;

FIG. 2 is a diagrammatic section view of a detail of a portion of a fluid dispenser head in a first embodiment of the present invention, shown in the closed position;

FIG. 3 is a view similar to the view in FIG. 2, shown in the open position;

FIG. 4 is a view similar to the view in FIGS. 2 and 3, showing a second embodiment of the present invention; and FIG. 5 is a view similar to the views in FIGS. 2, 3, and 4, showing a third embodiment of the present invention.

FIG. 1 is a diagrammatic view of a dispenser device that includes a reservoir 10 containing the fluid to be dispensed, on which reservoir there is assembled a dispenser member, specifically a pump 20, that is actuated by a pusher or a dispenser head that is provided with a spray orifice 31. In the embodiment in FIG. 1, the dispenser head is of the nasal type and it has a body 30 that is provided with an axial extension having an end that is provided with the spray orifice 31, said axial extension being for penetrating into the user's nostril. Naturally, the present invention also applies to other types of fluid dispenser device. In particular, the dispenser member 20 may be a pump of a different type, or it may even be a valve. In addition, the dispenser head may be of shape that is different, in particular with a spray orifice 31 that is directed in a direction other than the axial direction shown in FIG. 1, and in particular in a direction that is approximately perpendicular to the axial direction, as shown in FIG. 4.

In a conventional fluid dispenser device, upstream from the spray orifice 31, the dispenser head includes a spray profile that is generally formed of non-radial channels that connect the expulsion channel of the head to a central swirl chamber that is arranged directly upstream from the spray orifice. Such a spray profile gives rise to substantial shear stresses in the fluid by a succession of contractions and expansions, in particular at the non-radial channels and at the swirl chamber.

The present invention envisages replacing the spray profile with a system that is more suitable for use with biological active principles, such as proteins, peptides, hormones, enzymes, or similar, while guaranteeing that said biological active principles are sprayed properly. In particular, an object of the present invention is to provide fluid dispenser devices that are capable of satisfying a certain number of spraying performance characteristics, in particular with regard to spray particle size that preferably lies in the range 20 μm to 40 μm. Advantageously, no particle has a particle size that is less than 10 μm. In addition, the spray speed is preferably less than 10 m/s, and ideally about 1 m/s. The spray angle, i.e. the angle within which the various spray particles are situated after being dispensed through the spray orifice 31, is preferably less than 50°, and advantageously about 30°. The combination of these performance characteristics turns out to be particularly suitable for dispensing biological active principles having three-dimensional molecules that are large in size and relatively fragile, and thus subject to destruction in conventional spray profiles. Advantageously, these characteristics are applied to 50 to 100 microliter (μl) doses of fluid, and the nasal head is preferably inserted into the nostril over a depth of about 1 centimeter (cm). Naturally, these values are not limiting, and are only given by way of example.

In order to guarantee obtaining such spray characteristics or performance, the present invention provides vibration generator means 40, 140, 240 in the hollow body 30, 130, 230 of the dispenser head, said vibration generator means being actuated during the passage of the fluid coming from the dispenser member 20, in this instance preferably a mechanical pump, the actuation of said vibration generator means enabling said fluid to be sprayed finely through said spray orifice 31, 131, 231. Thus, it is the vibration generator means that are subjected to high-frequency stresses that make it possible to spray the fluid, said fluid no longer being subjected to the stresses, in particular the shear stresses, of conventional spray profiles.

Figures 2, 3:
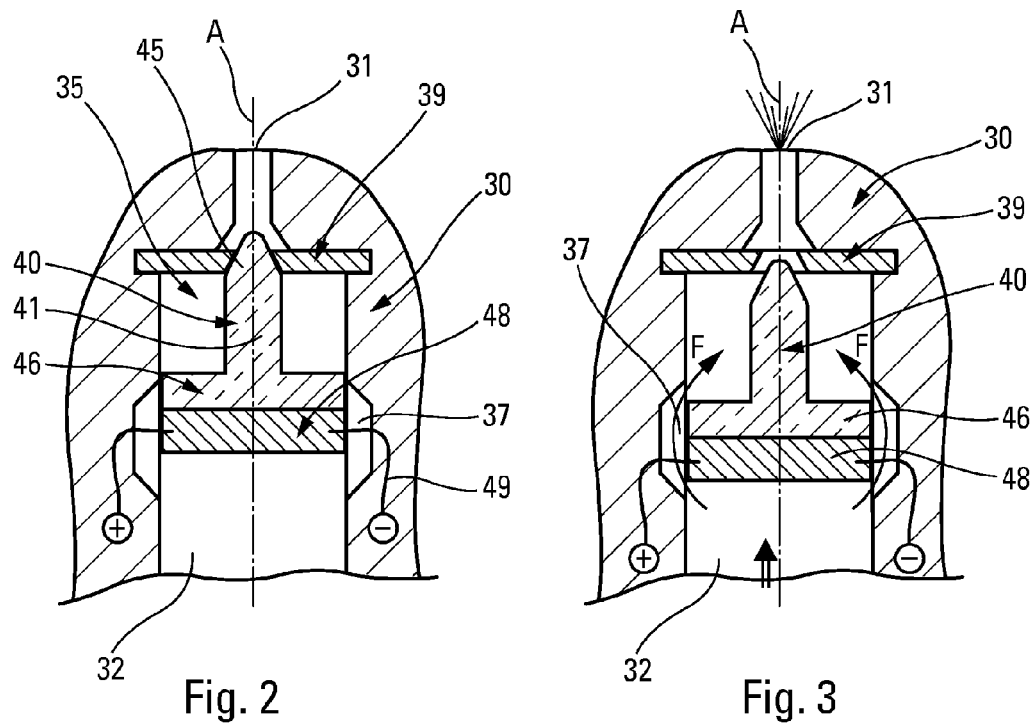

FIGS. 2 and 3 are diagrams showing a first embodiment of the present invention. In this first embodiment, the vibration generator means 40 include a pin 41. The pin 41 is preferably associated with a piezoelectric plate 48 that is connected to a power source 49, the excitation of the piezoelectric plate 48 causing said pin 41 to vibrate. At its downstream end, the pin 41 includes a tip 45 that is adapted to plug the spray orifice 31 of the dispenser head in leaktight manner when the tip is in the closed position. Preferably, such plugging in the closed position occurs by co-operation with a diaphragm 39 that is arranged directly upstream from said spray orifice 31, as shown in FIGS. 2 and 3. The pin 41 preferably slides in a channel that is substantially cylindrical and that is formed inside the body 30 of the dispenser head, the channel extending between the inlet orifice 32 and the spray orifice 31. Preferably, the inlet and spray orifices are situated axially along a longitudinal axis A, and said pin moves and vibrates along said same axis A. Advantageously, in its upstream portion, the pin 41 includes a disk 46 that is fastened on said piezoelectric plate 48, said disk having an outside diameter that is substantially equal to the inside diameter of said cylinder in which the pin moves. Thus, in the closed position, said pin 41 isolates a spray chamber 35, said tip 45 of the pin plugging the spray orifice 31 in leaktight manner, and said rear plate 46 of said pin closing a fluid passage 37 that is formed in the body 30 of said dispenser head. As can be seen in FIGS. 2 and 3, said fluid passage 37 is advantageously formed in a side wall of said head by a portion of greater diameter, so that in the open position shown in FIG. 3, the fluid can flow laterally around said pin 41, in particular around said piezoelectric plate 48 and said disk 46, as symbolized by the arrows F in FIG. 3. In the open position, the vibration of the pin 41 causes the fluid arriving in said spray chamber 35 to be dispensed in the form of fine droplets, without however exerting negatives stresses on the fluid, thereby making the device suitable for dispensing biological active principles.

FIG. 4 shows a second embodiment of the present invention. In this second embodiment, the vibration generator means 140 comprise a vibrating plate 148 that is arranged on an inside wall of the body 130 of said dispenser head. The fluid coming from the pump 20, preferably in the form of gel, comes to impact said vibrating plate 148, and the vibration of the vibrating plate 148 causes said fluid to be sprayed in fine droplets of a spray that is then dispensed through said spray orifice 131. In the embodiment in FIG. 4, the spray orifice is oriented approximately perpendicularly to the central axis of the head, which axis corresponds to the direction in which the fluid moves, in particular through the inlet orifice 132, as symbolized by the arrows F. In this embodiment, the vibrating plate 148 is preferably arranged in a plane that slopes relative to the direction F, advantageously at about 45°, so as to direct the droplets of fluid automatically and directly towards the spray orifice 131. The vibrating plate 148 is preferably formed of a piezoelectric material and it is connected to an electrical power supply 149 that is shown only very diagrammatically in FIG. 4 and that may be of any appropriate form. Thus, the jet of fluid that penetrates into the dispenser head through the inlet orifice 132 comes to impact the vibrating plate 148 which then fragments the jet into fine droplets of spray, without however subjecting said fluid to shear stresses and/or turbulences that are too great, and that are likely to be incompatible with dispensing fluids containing biological active principles. Advantageously, as shown in FIG. 4, a spray chamber 135 is formed directly upstream from the spray orifice 131, said vibrating plate 148 forming a wall of said spray chamber 135. Said chamber also includes a fluid inlet passage 137, preferably formed by a portion of smaller diameter in the body 130 of the dispenser head. The presence of the chamber between the vibrating plate 148 and the spray orifice 131 promotes the formation of the spray.

Figure 5:
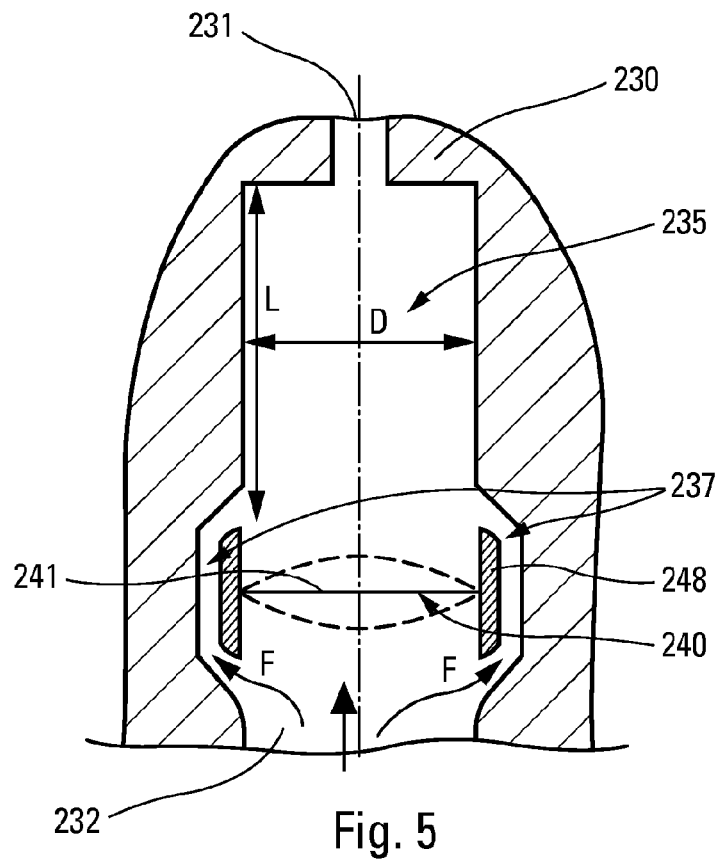

FIG. 5 shows a third embodiment of the present invention. In this third embodiment, the vibration generator means 240 comprise a vibrating diaphragm 241 that is arranged inside the body 230 of said dispenser head. In fact, this third embodiment makes provision for forming a Helmholtz resonator directly upstream from the spray orifice 231, so as to guarantee that the jet of liquid coming from the pump is sprayed. Advantageously, the Helmholtz resonator is formed by a resonance chamber 235 that is substantially cylindrical, having a length L and a diameter D. At its downstream end, said resonance chamber 235 opens out into the spray orifice 231 and, at its opposite end, it includes said vibrating diaphragm 241. Preferably, the diameter of the vibrating diaphragm is substantially equal to the diameter D of the resonance chamber 235. Naturally, the length and diameter dimensions L and D are selected so as to be less than the wavelengths involved, in particular the resonant wavelengths of the vibrating diaphragm 241, as is typical for a Helmholtz resonator. Thus, the Helmholtz resonator, in particular the volume of the resonance chamber 235, has the role of a hydraulic spring that pumps the liquid and contributes to fractioning the spray at the spray orifice 231, without however imposing on the fluid, shear stresses or other mechanical and physical stresses that are too great, making the device particularly suitable for dispensing biological active principles. As shown diagrammatically in FIG. 5, the dispenser head includes a portion 237 of greater diameter, forming a passage for the fluid, radially outside said vibrating diaphragm 241. The flow of the fluid at this location is symbolized by the arrows F.

Although the present invention is described above and shown with reference to three embodiments thereof, the invention is naturally not limited to those embodiments, but, on the contrary, any useful modification could be applied thereto by a person skilled in the art, without going beyond the ambit of the present invention, as defined by the accompanying claims.

The invention claimed is:

1. A fluid dispenser device comprising: a reservoir containing fluid; a dispenser member that is mounted on said reservoir; and a dispenser head that is mounted on said dispenser member, said dispenser head comprising an elongated portion extending along an axial direction of the dispenser head and configured to be inserted into a user's nostril, said dispenser head including a hollow body that defines a fluid passage between an inlet orifice, connected to said dispenser member, and a spray orifice; wherein a vibration generator mechanism is arranged in said passage upstream from said spray orifice, said vibration generator mechanism configured to be actuated while fluid is passing so as to spray said fluid finely through said spray orifice;

and wherein said vibration generator mechanism comprises a resonance chamber communicating at a downstream end with the spray orifice and having a vibrating diaphragm at an upstream end of the resonance chamber, and wherein the resonance chamber has a cross-sectional area taken in a direction orthogonal to the axial direction that is larger than a cross-sectional area of the spray orifice taken in the direction orthogonal to the axial direction, thereby defining a narrower passage through the spray orifice as compared with the resonance chamber, wherein said resonance chamber is substantially in the shape of a cylinder having a length and a diameter, each shorter than a resonance wavelengths of said diaphragm, said resonance chamber forming a Helmholtz resonator.

2. A device according to claim 1, wherein said vibration generator mechanism includes a piezoelectric material.

3. A device according to claim 1, wherein said diaphragm has substantially the same diameter (D) as said resonance chamber, said head including a passage for the fluid, which passage extends radially outside said diaphragm.

4. A device according to claim 1, wherein the fluid spray that is sprayed through said spray orifice has a mean particle size lying in the range 20 μm to 40 μm, and/or a spray speed that is less than 10 m/s, and/or a spray angle that is less than 50°.

5. The device according to claim 4, wherein the fluid spray that is sprayed through said spray orifice has a spray speed that is less than 5 m/s.

6. The device according to claim 4, wherein the fluid spray that is sprayed through said spray orifice has a spray speed that is less than 1 m/s.

7. The device according to claim 4, wherein the fluid spray that is sprayed through said spray orifice has a spray angle that is less than 30°.

8. The device according to claim 1, wherein the dispenser member is a pump or a valve.

9. The device according to claim 1, wherein the fluid spray that is sprayed through said spray orifice has a mean particle size lying in the range 20 μm to 40 μm, and/or a spray speed that is less than 1 m/s, and/or a spray angle that is less than 30°.

10. The device according to claim 1, wherein the spray orifice is located at an end of the dispenser head and configured to direct the spray in the axial direction of the dispenser head.

11. The device according to claim 1, wherein the spray orifice is located near an end of the dispenser head and configured to direct the spray in a direction substantially perpendicular to the axial direction of the dispenser head.

* * * * *